United States Patent
Gibson et al.

(10) Patent No.: US 10,292,717 B2
(45) Date of Patent: *May 21, 2019

(54) SYSTEMS AND METHODS FOR ALTERING THE SURFACE OF A BONE

(71) Applicant: Smith & Nephew, Inc., Memphis, TN (US)

(72) Inventors: Luke Andrew Gibson, Southaven, MS (US); Jeffrey A. Sharp, Salt Lake City, UT (US)

(73) Assignee: SMITH & NEPHEW, INC., Memphis, TN (US)

(*) Notice: Subject to any disclaimer, the term of this patent is extended or adjusted under 35 U.S.C. 154(b) by 431 days.

This patent is subject to a terminal disclaimer.

(21) Appl. No.: 15/163,354

(22) Filed: May 24, 2016

(65) Prior Publication Data
US 2016/0262772 A1 Sep. 15, 2016

Related U.S. Application Data

(63) Continuation of application No. 13/816,166, filed as application No. PCT/US2011/047907 on Aug. 16, 2011, now Pat. No. 9,345,495.
(Continued)

(51) Int. Cl.
*A61B 17/16* (2006.01)
*A61B 34/10* (2016.01)
(Continued)

(52) U.S. Cl.
CPC ...... *A61B 17/1662* (2013.01); *A61B 17/1659* (2013.01); *A61B 17/17* (2013.01);
(Continued)

(58) Field of Classification Search
CPC . A61B 17/16; A61B 17/1662; A61B 17/1659; A61B 17/17; A61B 17/1703; A61B 34/10
See application file for complete search history.

(56) References Cited

U.S. PATENT DOCUMENTS 5,653,714 A * 8/1997 Dietz ............... A61B 17/1764
606/87
9,345,495 B2 * 5/2016 Gibson ............ A61B 17/1746
(Continued)

FOREIGN PATENT DOCUMENTS

CN 1627920 A 6/2005
JP 05269140 A 10/1993
(Continued)

OTHER PUBLICATIONS

European Examination Report; European Patent Office; European Application No. 11818659.2; dated May 3, 2016; 7 pages.
(Continued)

*Primary Examiner* — Christopher Beccia
(74) *Attorney, Agent, or Firm* — Pepper Hamilton LLP (57) ABSTRACT

Systems and methods to provide patient-specific cutting blocks that allow for bone resurfacing procedures, such as milling or burring, with simplified devices. A computer assisted surgical cutting block is produced having a surface region that matches with the surface region of a patient's bone to be altered. A cutting tool may be provided having a contoured bone mating surface and a contoured and patient-specific shaped cutting guide surface located in a plane above the bone mating surface. One or more channels are provided in the cutting block, and as the surgeon moves the cutting tool (a milling or burring, for example) in the channels, the tool cuts the bone both laterally along the surface of the bone and vertically into the bone according to the cutting guide surface and other preselected surface features of the cutting block.

20 Claims, 9 Drawing Sheets

Related U.S. Application Data (60) Provisional application No. 61/373,967, filed on Aug. 16, 2010.

(51) Int. Cl.
*A61B 17/17* (2006.01)
*A61B 17/56* (2006.01)

(52) U.S. Cl.
CPC ........ *A61B 17/1703* (2013.01); *A61B 17/175* (2013.01); *A61B 17/1746* (2013.01); *A61B 17/1764* (2013.01); *A61B 34/10* (2016.02); *A61B 17/1739* (2013.01); *A61B 2017/568* (2013.01); *A61B 2034/108* (2016.02)

(56) References Cited

U.S. PATENT DOCUMENTS

| | | | |
|---|---|---|---|
| 2006/0122616 A1* | 6/2006 | Bennett | A61B 17/1764 606/87 |
| 2006/0293682 A1* | 12/2006 | Justin | A61B 17/1615 606/88 |
| 2008/0009874 A1 | 1/2008 | Meridew et al. | |
| 2008/0058949 A1 | 3/2008 | Dees et al. | |
| 2008/0112996 A1 | 5/2008 | Harlow et al. | |
| 2008/0287953 A1* | 11/2008 | Sers | A61C 1/084 606/87 |
| 2009/0012526 A1 | 1/2009 | Fletcher | |
| 2009/0088756 A1 | 4/2009 | Anderson | |
| 2009/0088758 A1* | 4/2009 | Bennett | A61B 17/155 606/82 |
| 2009/0254093 A1 | 10/2009 | White et al. | |
| 2010/0168866 A1 | 7/2010 | Shih | |
| 2011/0015639 A1 | 1/2011 | Metzger et al. | |
| 2011/0106093 A1 | 5/2011 | Romano et al. | |

FOREIGN PATENT DOCUMENTS

| | | | |
|---|---|---|---|
| JP | 11504532 A | 4/1999 | |
| JP | 2010502389 A | 1/2010 | |
| JP | 2011505922 A | 3/2011 | |
| JP | 2012502742 A | 6/2012 | |
| JP | 6005645 B2 | 10/2016 | |
| WO | 1996025114 A1 | 8/1996 | |
| WO | 2006/135462 A2 | 12/2006 | |
| WO | 2008112996 A1 | 9/2008 | |
| WO | 2009076296 A1 | 6/2009 | |
| WO | 2010071739 A1 | 6/2010 | |

OTHER PUBLICATIONS

Korean Office Action; Korean Intellectual Property Office; Korean Patent Application No. 10-2013-7006749; dated Sep. 13, 2017; 18 pages.
Japanese Notice of Reasons for Rejection; Japanese Patent Office; Japanese Application No. 2016-123442; dated May 8, 2017; 6 pages.
Mexican Office Action; Mexican Patent Office; Mexican Patent Application No. MX/a/2017/009312; dated Feb. 6, 2018; 5 pages.
European Examination Report; European Patent Office; European Application No. 11818659.2; dated Mar. 8, 2018; 4 pages.
Russian Office Action; Russian Patent Office; Russian Patent Application No. 20130109813; dated May 14, 2015; 4 pages.
Russian Office Action; Russian Patent Office; Russian Patent Application No. 20130109813; dated Sep. 8, 2015; 8 pages.
Japanese Office Action; Japanese Patent Office; Japanese Patent Application No. 2013-524926; dated Jun. 15, 2015; 5 pages.
Chinese Search Report; Chinese Patent Office; Chinese Patent Application No. 201180050038.4; dated Apr. 16, 2015; 4 pages.
Chinese Office Action; Chinese Patent Office; Chinese Patent Application No. 201180050038.4, dated Apr. 27, 2015; 10 pages.
Chinese Office Action (Second); Chinese Patent Office; Chinese Patent Application No. 201180050038.4; dated Dec. 22, 2015; 8 pages.
First Examination Report; Australian Patent Office; dated Jul. 3, 2013; 2 pages.

* cited by examiner

SYSTEMS AND METHODS FOR ALTERING THE SURFACE OF A BONE

CROSS-REFERENCE TO RELATED APPLICATIONS

This application is a continuation of U.S. patent application Ser. No. 13/816,166 filed Sep. 25, 2013, which is a U.S. national phase filing of International Application No. PCT/US2011/047907 filed Aug. 16, 2011, which claims the benefit of U.S. Provisional Application No. 61/373,967 filed Aug. 16, 2010, the disclosures of each of these applications hereby incorporated by reference in their entirety.

BACKGROUND

Many patients suffer from orthopedic injuries or bone degenerative conditions that arise during exercise or over time during normal wear and tear. In some cases, the patient's bone becomes warped or has growths or other lesions that arise from extensive use of the bone. Athletes, in particular, may experience that condition when doing heavy workouts, especially in the area of the femoral connection to the acetabulum. In femoroacetabular impingements, an area around the femoral head or the acetabular rim bulges with excess bone growth to the point where the femoral head is impinged when moving about the acetabulum, a condition that is often very painful. A cam impingement results when an abnormality on the surface of the femoral head or neck contacts the rim of the acetabular socket. A pincer impingement results when a patient's acetabulum is deeper than is normal, and the deep socket restricts full movement of the femoral head.

Orthopedic surgeries are performed to resurface bones, such as knees, hips, shoulders, ankles, and elbows that are impinged or otherwise damaged by stress and wear or injury. In hip and femoral resurfacing procedures, treatment approaches may involve milling or burring the femoral head to relieve impingement. The milling and burring is often done by free-hand, based on visual estimates of the location, depth and dimension of the bone. The size and fit between the resurfaced bone and the acetabulum or other joint can vary—in some cases being too loose, and in others too tight. Similarly, in surgeries that involve shaping a bone to receive an implant, free-hand cutting may be too imprecise leaving the bone location too large or small to properly seat the implant.

Computer assisted methods have been developed that provide graphical images of bones and use software that allows the surgeon to cut the bone and install an implant to fit a surgical site more precisely. During a computer-assisted surgery (CAS), a surgeon uses a visual image of the patient's anatomical site to create an implant that fits the site or to alter the site to receive an implant. Example CAS systems are found in U.S. application Ser. No. 12/240,992 and U.S. application Ser. No. 12/120,547. In some cases, the physician uses a cutter or other surgical tool to resect the bone. In most systems, the surgical tool is guided by a computer assisted system which requires a complex tool registration system that can be difficult to use and expensive. Improved methods and systems are needed for resurfacing bone regions particularly in patients with femoroacetabular impingements and other bone conditions.

SUMMARY

Disclosed herein are systems and methods for guiding the use of a cutting tool, such as a burring or milling tip, to alter the surface of a bone in a patient. The systems and methods include using a patient matched block that is formed from images taken of the patient's bone, and then creating a mold that has a surface that fits with a portion of the bone to be altered. The block includes one or more cutting zones that align with the region to be altered, such that a cutting tool can be guided within the cutting zone to resect or otherwise resurface the desired area of the bone to achieve the desired surface structure and shape.

In certain implementations, a cutting block is provided for guiding the alteration of a bone surface. The cutting block includes a first cutting guide forming a two dimensional lateral boundary for a cutting tool and a second cutting guide forming a depth boundary for the cutting tool.

In certain embodiments, the cutting block includes a housing having a longitudinal axis, a collar having a distal end, a proximal end, and a bone mating inner surface disposed along the longitudinal axis, and a plurality of walls that extend above the collar. A plurality of surface regions are disposed on the bone mating surface, which surface regions have a plurality of surface characteristics corresponding to respective surface features on the bone. The respective surface features may be derived from a computer image of the bone and included in a bone model. The housing also has a cutting guide with a channel that extends between the plurality of walls in a plane substantially parallel with the longitudinal axis. An entry port is disposed along a surface of at least one of the walls through which a cutting tool passes to enter the channel.

In certain embodiments, the housing is configured with a plurality of surfaces that match bone surfaces of the patient. In certain implementations, the collar has a bottom opening that extends from the proximal end to the distal end of the collar and is configured to receive a patient's bone. The bone enters the opening and rests against the inner surface, which includes the surface regions with a plurality of surface characteristics corresponding to respective surface features on the bone. In certain implementations, the bone mating surface has one or more pre-formed contours that matches one or more corresponding surface features of the bone.

In certain embodiments, the plurality of walls has an upper boundary wall with a surface that is contoured to match a pre-selected bone surface. The upper boundary wall surface can serve as a guide, e.g., a depth guide, to guide a milling or burring tool as it passes laterally along the surface of the bone during resurfacing or resection. In certain implementations, the upper boundary surface slopes from the proximal end of the housing to the distal end of the housing.

The block is also configured to guide the lateral cutting of the tool. In certain implementations, the channel has a plurality of laterally extending channels. The channels may be exposed above the surface of the upper boundary so that the cutting tool can be manipulated laterally along the bone surface but remain within the channels for a precise cut. The channels are accessible through an entry port disposed along the plurality of walls. A flange may be disposed below the entry port and extend into the channel or other opening.

In certain embodiments, one or more washer inserts are disposed within the channel. Each washer insert has a washer opening that aligns with the channel and, where a plurality of washer inserts is used, another washer opening. The block is connected to the bone surface by pins or anchors and includes a plurality of holes disposed in the housing to receive the pins or anchors.

The cutting block may be incorporated in a kit or other system for altering a bone surface. The kits or systems may include a pre-formed image of a selected bone surface and a cutting tool with a portion that fits within the channel or other guide feature of the cutting block. A plurality of cutting blocks may also be included. For instance, a first of the plurality of blocks includes a trough with a first depth and a second of the plurality of blocks includes a trough with a second depth different than the first depth. The first and second blocks may be stacked together. For instance, the first of the plurality of blocks may fit within the second of the plurality of blocks. The washer inserts and other components described herein may also be included. In certain implementations, a plurality of washer inserts are provided, each having a washer opening, the inserts sized and configured to fit within the channel of a cutting block, and each washer opening receiving a portion of the cutting tool.

The cutting tool can also be configured to fit with the dimensions of the cutting block, to provide a more accurate and elegant cut. In certain implementations, the cutting tool has a first depth, and the cutting block has an opening, such as a channel, with a depth that is substantially the same as the first depth. In use, the cutting tool is inserted into the cutting block via the opening and, when so inserted, rests with a shoulder or other surface slightly above the opening, so the tool can move laterally within the opening but is confined vertically to remain within the opening. In certain implementations, the cutting tool has a rotary tip that allows it to perform milling or burring on the surface of the bone.

Methods of use are also contemplated. In certain embodiments, a method of altering a bone surface includes receiving an image of the surface of a bone to be altered, the image identifying a surface characteristic comprising one or more of a contour, slope, or landmark on the bone. A user identifies a region of the bone surface to be removed from the bone and uses the image to generate a cutting guide. The cutting guide has a channel and an interior surface with a plurality of surface features, each surface feature corresponding to a surface characteristic on the image. The cutting guide is applied to the bone by aligning the surface features with the corresponding surface characteristics, until the channel sits above and extends substantially to the region to be removed. A cutting tool is inserted through the channel into contact with the region. The cutting tool is then manipulated laterally and depth-wise through the channel to resurface the bone along its surface.

Certain methods of resecting a bone surface contemplate preparing a cutting guide having a bone contacting inner surface that is configured to mate with the bone surface, and an upper surface having a contoured configuration corresponding to a desired bone surface configuration. In certain implementations, the bone contacting inner surface has one or more features configured to match a corresponding surface characteristic existing on the bone prior to cutting the bone. The upper surface is formed to correspond to the surface configurations the bone should have when the surgery is complete, and is preferably spaced away from the inner surface.

The cutting guide is applied to the bone surface and extended along the contoured upper surface while cutting the bone surface (e.g., an impinged surface area) according to the desired bone surface configuration. The resulting bone, after being cut, thus has the desired bone surface configuration. The cutting tool may pass within a channel of the guide and cut the bone in lateral directions, as well as vertical directions (e.g., along the upper surface). The cutting tool may also include a flange that is braced against a surface of the cutting guide while the bone is being cut. The flange thereby assists in modulating the depth of the cuts that can be made. The bone surface may be milled or burred through the channel of the guide.

Variations and modifications of these embodiments will occur to those of skill in the art after reviewing this disclosure. The foregoing features and aspects may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

Further features, aspects, and advantages of various embodiments are described in detail below with reference to the accompanying drawings.

BRIEF DESCRIPTION OF THE DRAWINGS

The accompanying drawings, which are incorporated in and form a part of the specification, illustrate embodiments and together with the description, serve to explain various examples of the disclosed methods and systems. In the drawings.

DETAILED DESCRIPTION OF EXAMPLE EMBODIMENTS

The figures illustrate certain implementations of systems and methods used to prepare patient matched cutting guides for conducting bone resurfacing, for example milling or burring to treat cam impingement. The cutting guides help a surgeon more accurately locate the proper region on the bone to cut and provide a lateral guide, a depth guide (or both) for making the resection cuts. The cutting guide itself is formed to custom fit the patient's bone by taking an image of the bone and using that image to create a cutting block to place on the bone during resection and resurfacing. The patient-specific cutting guide also helps improve the surgical process compared to a free-hand process. In certain implementations, the patient-matched cutting guide includes an inner surface that conforms to the patient's bone and a port or opening that receives a burring or milling tool of a medical device for cutting within the guide.

Figure 1:
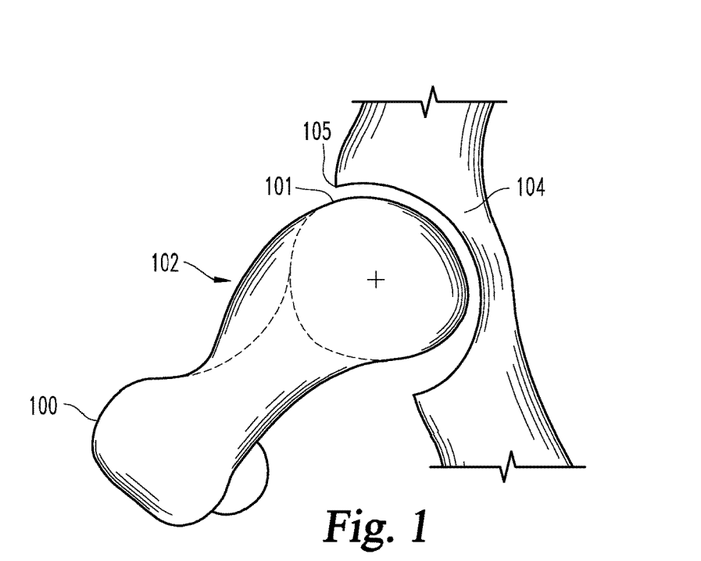
FIG. 1 depicts a femur having an impingement region and a femoral head that fits within an acetabulum.

Referring to the accompanying drawings in which like reference numbers indicate like elements, FIG. 1 depicts an example of a cam impingement in a case where the patient's femur 100 is disposed with femoral head 101 within the acetabulum 104 of the hip. The femoral head 101 has an impinged region 102. With that condition, the patient will often experience pain when the femur 100 rotates or operates within the acetabulum 104 because the impinged region 102 bumps against the acetabular rim 105.

FIGS. 2A-2E depict various views of an embodiment of a cutting block 200 that is structured to custom fit the patient's femur 100 on or near the femoral head 101. The cutting block may be made of strong polymer or other suitable material and guide the user in performing bone resection or resurfacing. As shown, the cutting block includes a housing having a collar 202 that extends along a longitudinal axis 201 and has a proximal end 202a and a distal end 202b. The collar also includes a lower opening 205, parallel to the longitudinal axis 201, through which the femoral head 101 or other bone is fitted. The collar 202 also includes an inner bone mating surface 204 that is custom fitted with the region of the femoral head 101 where, for example, the impingement region 102 exists.

Figures 2A, 2B:
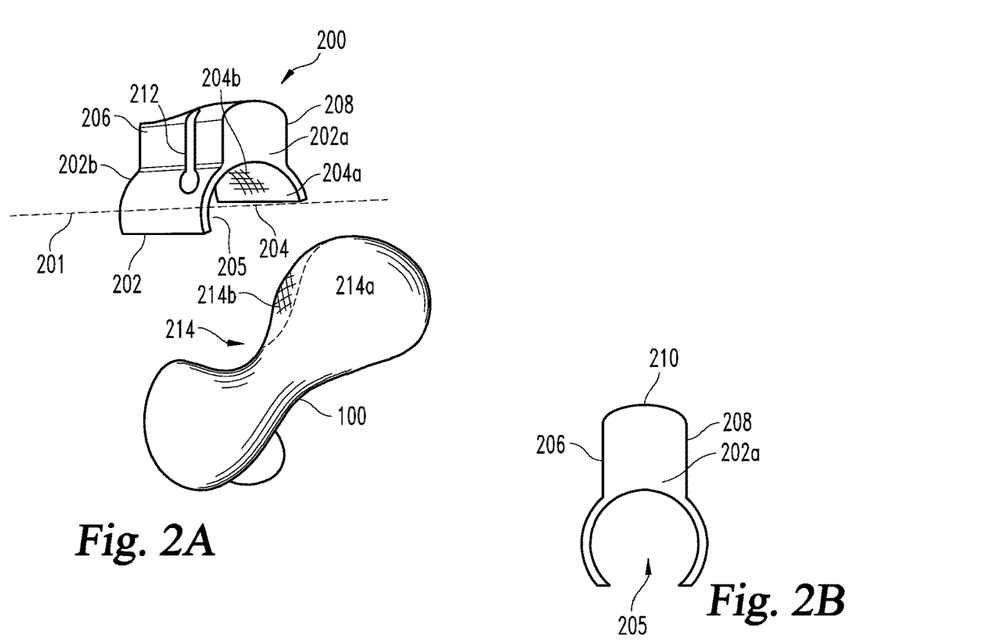
FIGS. 2A-2E depict an embodiment of a cutting block that is configured to fit specifically to the femoral head shown in FIG. 1.
Figure 2C:
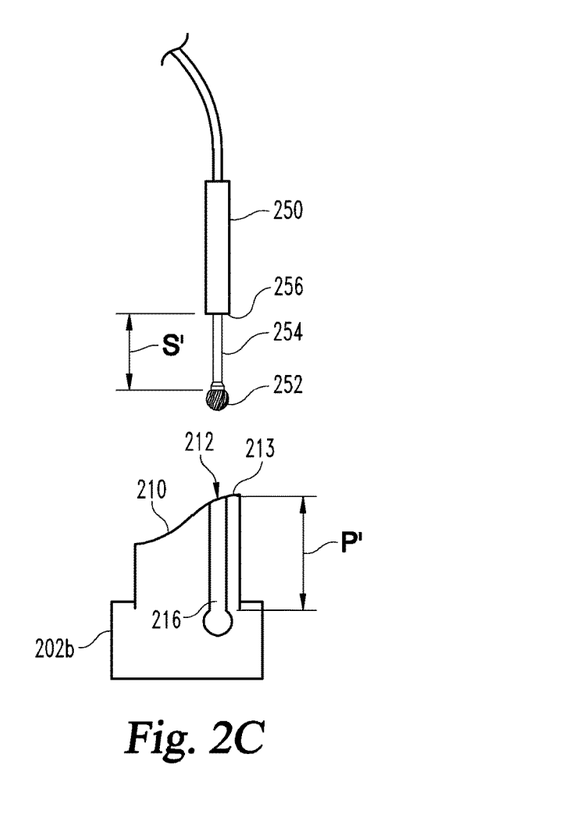
Figure 2D:
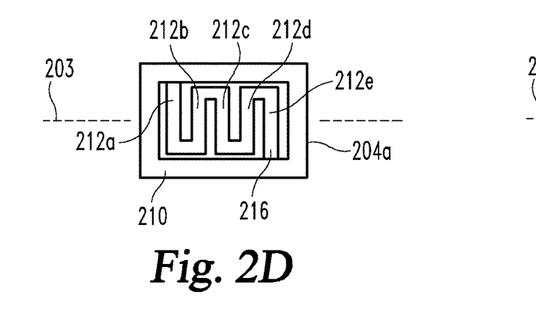
Figure 2E:
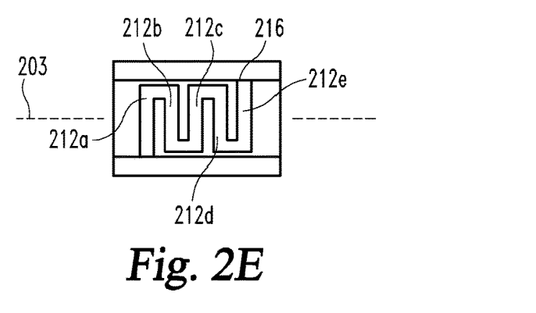

The cutting guide 200 also includes an upper housing with a plurality of walls 206 and 208 that rise above the inner bone mating surface of the collar and are joined by an upper boundary surface 210. A guide channel 212 is disposed within the cutting block 200 between the two walls 206 and 208. The guide channel 212 includes an entry port 216 disposed along a surface of the wall 206. A cutting tool (such as a burring or milling tool having a rotary tip) may be inserted within the cutting channel through the entry port 216 to gain access to the bone beneath the channel 212. An example cutting tool that may be used is shown in FIG. 2C, illustrating a milling tool 250 having a milling head 252 with a rotary tip and a shaft 254 that drives the rotation of the tip. As shown, the entry port 216 has a depth dimension P' that is slightly shorter than the length of the shaft 254 (S'). Thus, when the milling tool 250 is inserted within the entry port 216, the lower shoulder 256 of the tool 250 rests on or just slightly above the upper shoulder 213 of the channel 212, which keeps the tool in the channel. The tool can move laterally and vertically, but only as guided within the channel. The precise fit between the tool and the channel thereby allows a more precise milling or burring of the bone surface.

As indicated, the cutting block is prepared to custom fit to the area of the patient's femur or other bone to be resurfaced so the cutting channels will be placed in the proper location on the bone. As shown in FIG. 2A, the inner bone mating surface 204 of the collar 202 has a plurality of regions with surface characteristics that correspond with respective surface features on the impinged bone. As shown, for example in FIG. 2A, the inner mating surface 204 includes a first concave region 204b that is prepared with particular surface characteristics, such as curvature, contouring, surface indentations and recesses to mirror and match with features of the bone to be resurfaced. For instance, the first region 204b custom fits the rise area 214b in the femur. Similarly, the smooth surface 204a of the inner mating surface 204 is prepared to contour and fit in a patient-matched interface with the smooth contoured surface 214a of the femur.

In certain implementations, the cutting block with the patient-specific collar is prepared using a graphical or other image of the bone to be resurfaced. For example, the surgeon or other technician takes a CAT scan, MRI, or other image of the bone surface, then uses that image with a processor to generate a computer image of the surface of the bone. The computer image is manipulated to produce a model of the bone surface in a desired resurfaced configuration. The model will depict contouring, slope, surface features and other desired attributes that will be applied to the bone through the resurfacing process. CAD software or other design tools may then be used to design a cutting guide that has a surface that aligns and fits with the precise surface area of the bone. The cutting guide will preferably include one or more channels that guide the cutting tool to more easily create the desired bone resurfacing. After preparing the CAD model of the cutting guide and the desired resurfacing configurations, a physical embodiment is produced, such as cutting block 200, where the inner bone mating surface 204 is configured to correspond and specifically mate with the impingement region 102 of the femoral head 101, and the cutting channels and upper surface are custom-configured with a lateral guide and a depth guide that guide the cutting tool, ultimately preparing a bone cut that results in a desired surface configuration. That desired surface configuration allows the femoral head (or other relevant bone) to extend and rotate within the neighboring joint without impingement.

In particular, as shown, the channel 212 has a plurality of laterally extending channels 212a-212e that extend in a plane having a channel axis 203. The channel axis 203 extends generally above and in parallel with the longitudinal axis 201 of the collar. The channel 212 having its plurality of internal channels 212a-212e thereby permits a cutting tool to mill, burr, or otherwise trim the surface of a bone along the plane that extends parallel along the longitudinal axis 201 of the collar. Moreover, the internal channels 212a-212e extend back and forth through the channel 212 along the channel axis 203, thereby allowing the technician or the surgeon to apply the milling tool within the channels along the channel axis 203. This allows the milling or burring or other resurfacing of the bone in two dimensions, laterally along the surface the bone.

Figure 3:
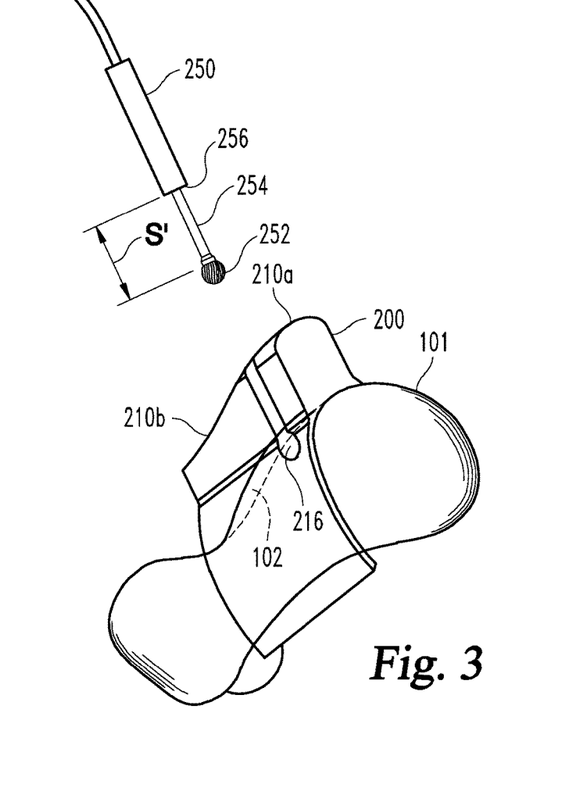
FIG. 3 depicts the cutting guide of FIG. 2 fitted to the femoral head of FIG. 1.

The cutting block is also structured with a depth guide for the cutting tool. FIG. 3, depicts the cutting block 200 fitted to the femoral neck and the femoral head 101, and a cutting tool 250 having a milling head 252 on a distal tip and a shaft 254 that turns the milling head. The cutting block 200 may be secured to the femoral neck and head by a press-fit interaction in which the block 200 snaps onto and remains secured to the bone, or the block 200 may include anchoring holes through which pins are placed into the bone to secure the block to the bone. As shown, the upper boundary surface 210 of the cutting block is sloped from the proximal end 210a to the distal end 210b. The upper boundary surface 210 is configured with the same contouring, slope, and other features of the desired resurfaced configuration of the femoral head 101. In use, the cutting tool 250 is inserted within the channel 212 by inserting the head 252 and shaft 254 through the entry port 216, and then advanced within the channels. The slope (and its contouring and other features) of the upper boundary surface 210 provides a depth guide for the cutting tool, such that when passing through the channels 212a-212e, the cutting guide will also move vertically up or down, as it passes from proximal to distal ends, thereby extending the tip 252 deeper or more shallow, according to the upper boundary surface 210, so that when the milling process is completed and the cutting block is removed, the slope, contouring, and other features of the resurfaced bone will match or at least closely approximate the slope, contouring, and surface features of the upper boundary surface 210. The slope and contouring of the upper boundary surface 210, coupled with the laterally extending channels 212a-212c of the cutting guide 200 thus provide a combined lateral guide and depth guide for the cutting tool, for more precise alteration of the bone surface.

Figure 4:
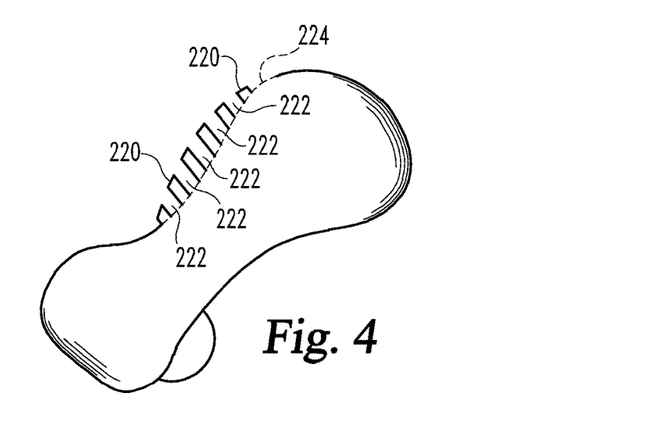
FIG. 4 depicts the femur of FIG. 1 after cutting using the cutting guide of FIG. 3.

Additional interim or other bone processing steps may also be performed. FIG. 4 depicts the resected femur 100 after the cutting block has been removed. As shown, a plurality of remnants 220 are left in the bone surface of the femoral head 101. Those remnants 220 are interspersed between a plurality of voids 222 which correspond to the channels 212a-212e. As the milling tool or burring tool is passed through the channels 212, the removed bone is eliminated, leaving the voids 222 while portions of the uncut bone 220 remain in the areas between the channels. After removing the collar 200, the operator can use a subsequent burring or milling tool to eliminate the remnants 220. As also shown in FIG. 4, after removing the remnants 220, a sloped surface 224 (hatch lines) is left behind in the bone. This sloped surface corresponds to the sloping and contouring of the upper boundary surface 210, as discussed above.

Figure 5A:
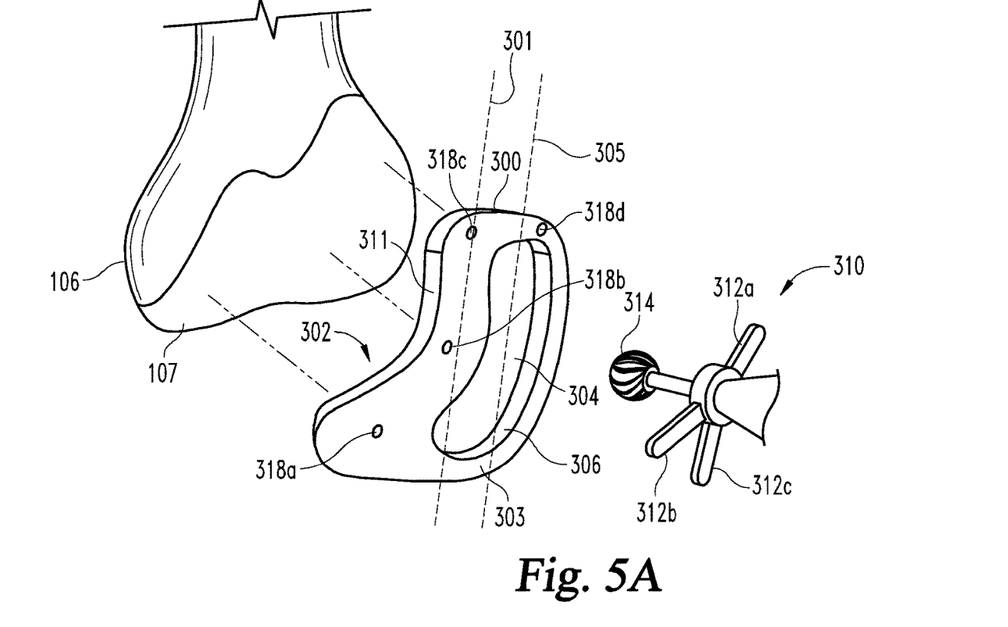
FIGS. 5A-5B depict an embodiment of a cutting block configured to mate with and mount upon a femoral head, and a burring or milling tool for conducting bone resection through an opening in the block.
Figure 5B:
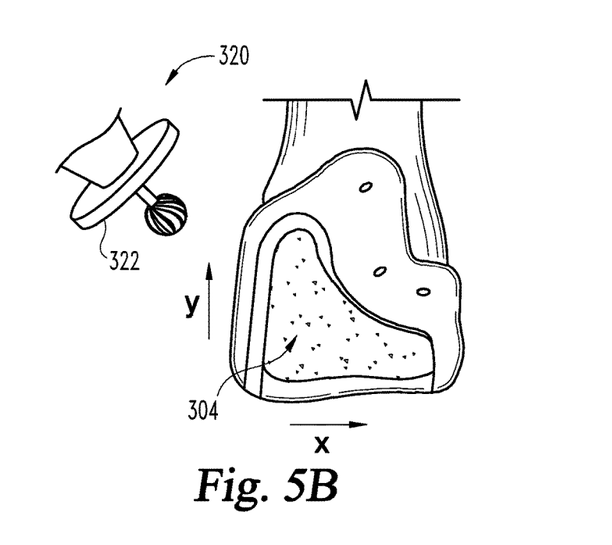

FIGS. 5A-5B depict an alternative embodiment of a cutting block 300 fitted to a femur 106 about a region 107 that is intended to be milled or burred to resurface the bone. The cutting block 300 includes an inner bone mating surface 302 (formed for example by a patient-matched process) with a plurality of surface regions with characteristics that correspond to respective surface features on the femur 106 in the region 107. The cutting block 300 also includes side walls 311 and an upper surface wall 303 that has an entry port to a channel 304 within which the burring or milling tool 310 is inserted.

The cutting block 300 has a longitudinal axis 301. The channel 304 also has a channel axis 305, which lies in a plane that generally includes the longitudinal axis 301 of the block 300. In use, the distal tip 314 of the milling tool 310 extends within the channel 304 along the axis 305 to mill or burr the bone surface. The tool is free to move within the boundary created by the channel, in both longitudinal and lateral directions.

FIG. 5B illustrates longitudinal and lateral directions by arrows X and Y, respectively, and milling or burring within the channel 304 allows a wide two-dimensional range within which to sculpt the bone. A flange 306 is disposed within the channel 304 to stop the depth penetration of the tool 310 when its bracing arms 312a-312c reach the flange 306 (or when the disc shaped bracing surface 322 rests against the flange 306). Thus, the flange provides a depth guide for the resurfacing process, while the channel 304 provides a lateral guide for the resurfacing process. Alternative bracing arm configurations may also be used, including the disc 322 shown in FIG. 5B. This three-dimensional cutting block, which is patient-matched, thus provides depth and lateral alignment capability to facilitate more precisely sculptured or resurfaced bone. As shown, a plurality of pinholes 318a-318d are provided to anchor the cutting block to the bone.

Figure 6A:
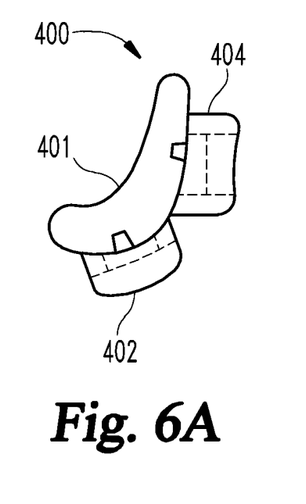
FIGS. 6A-6B depict a system for conducting bone milling with a plurality of cutting blocks mounted to a patient's bone.
Figure 6B:
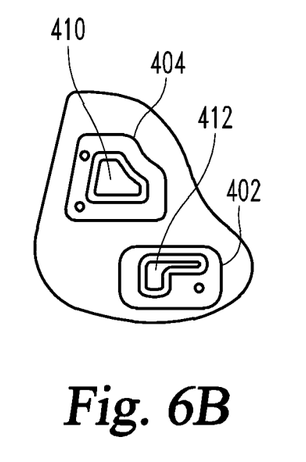

The cutting blocks described above can be provided in kits or in surgical systems that allow customized resurfacing of a patient's bone. In certain implementations, the kits and systems include a plurality of cutting blocks. As shown in FIGS. 6A-6B, a cutting guide system 400 includes a first cutting block 402 and a second cutting block 404, which may include one or more of the cutting blocks described above. The cutting guide system 400 also includes an inner surface 401 that is patient-matched to correspond to and mate precisely with the surface of the bone to be resurfaced. Milling tools may be inserted within the openings 410 and 412, respectively, of the cutting blocks for more complex bone preparations. A plurality of these blocks with different milling shapes and depths can be provided, as desired.

Figure 7:
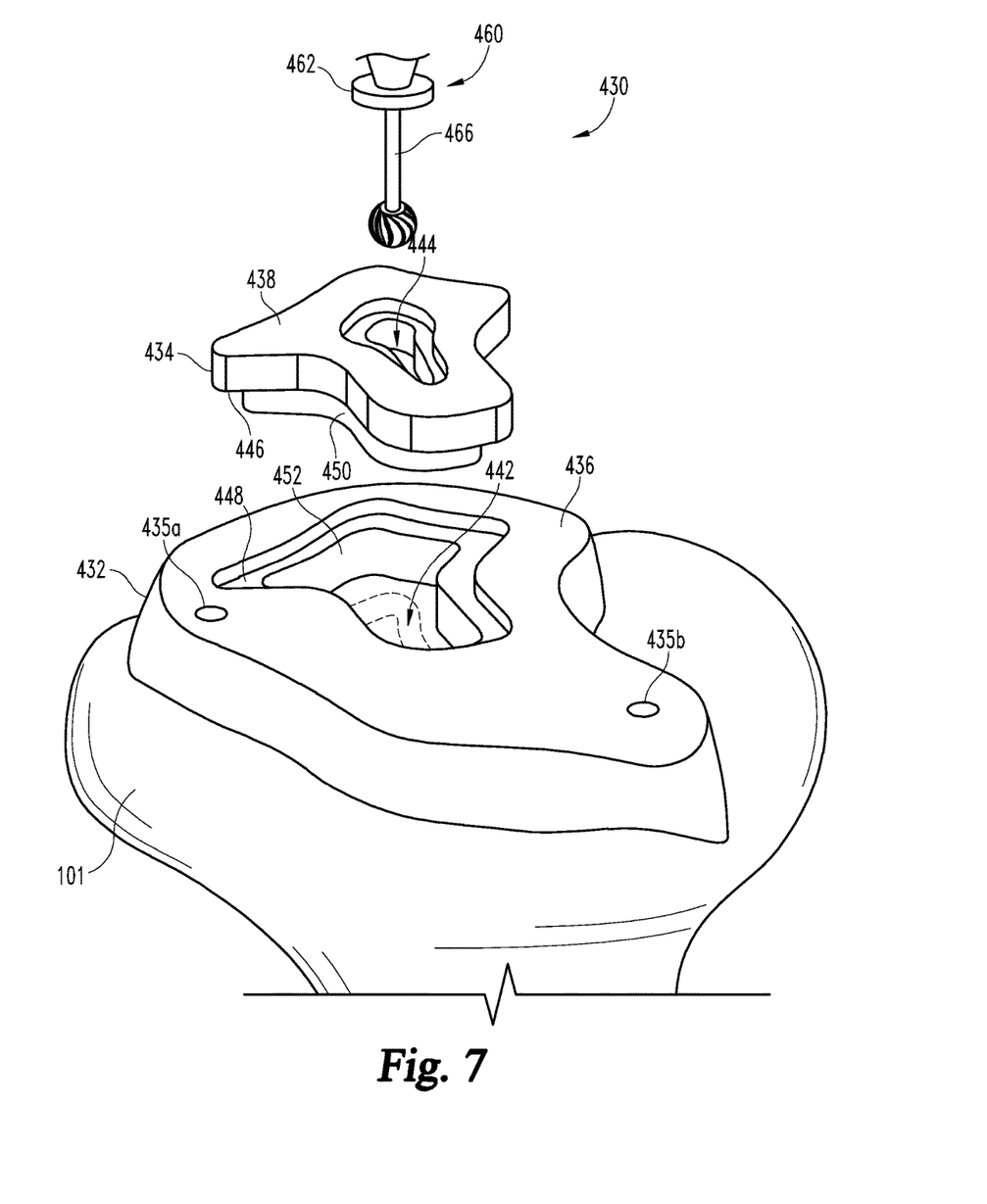
FIG. 7 depicts an embodiment of a cutting block having a plurality of bone mounts mated together and having a common opening for receipt of a cutting tool.

FIG. 7 depicts an implementation of a cutting guide system 430 having a plurality of blocks 432 and 434 that stack together, with upper block 434 configured to be seated within the lower block 432. The lower block 432 is anchored to femoral head 101, the distal end of a femur, or to another suitable bone surface through anchoring holes 435a and 435b. The upper cutting block 434 is then seated within the opening 442 of the lower block 432. In particular, the shelf 446 of the upper block 434 sits on the ledge 448 of the lower block 432, and extension 450 of the upper block aligns with extension 452 of the lower block. This arrangement aligns the opening 444 of the upper block 434 with the opening 442 of the lower block 432. A cutting tool 460 can then be extended through the openings 444 and 442 to mill a first layer of bone from the desired part of the femoral head. The milling of the first layer will be confined by the dimensions of the opening 444 and depth of upper block 434. In particular, milling can proceed until the disc 462 of the cutting tool 460 reaches the upper boundary surface 438 of the upper block 434, with the distal tip 464 of the cutting tool 460 penetrating into the bone and extending laterally within the boundary of the opening 444. After milling this first layer, the upper block 434 is removed and the milling continues to a second layer. The second layer is similarly milled—laterally within the opening 442 and vertically until the disc 462 reaches the upper surface 436 of the lower block 432. The opening 442 is laterally wider than the opening 434, and the second milling surface located within the bone matches the lateral perimeter of the opening 442. The upper surface 436 of the lower block 432 could be sloped or tapered, contoured, and otherwise shaped according to the surface characteristics desired in the resulting resurfaced bone area, as discussed above with respect to FIGS. 2A-2E.

In certain implementations, stacked blocks are configured to reduce over-burring when blocks are removed and the opening provided is wider. For example, in FIG. 7, removal of the upper block 434 leaves a wide opening 442 in the lower block 432, and the depth of the cutting tool 460 is not constrained if the tool is placed in the center of the opening 442, as the disc 462 is not wide enough to contact the upper surface 436 of the block 432. To prevent the cutting tool 460 from advancing too deep into the center of the opening 442, an insert having a shape matching that of the opening 444 in the upper block 434 can be provided to cover the portion of the bone that is milled through opening 444. The insert is pinned into the bone, and then the upper block 434 is removed. With the insert in place, only the bone that is milled through the wider opening 442 is exposed, and the disc 462 can contact both the insert and the upper surface 436 to avoid advancing the cutting tool 460 beyond a desired depth into the bone.

Figure 8:
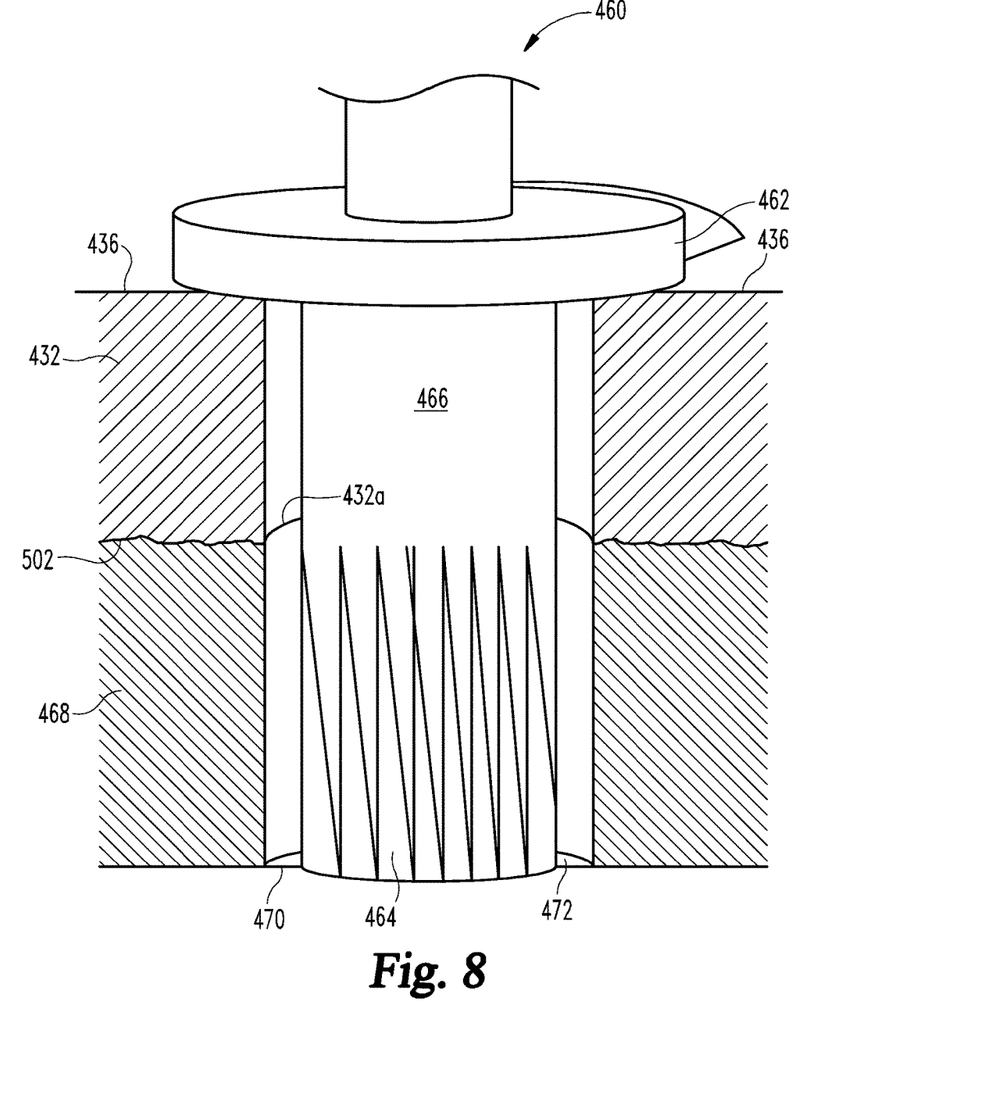
FIG. 8 depicts a cross sectional view of a burring tool disposed within an opening and a cutting block for conducting bone resurfacing.

FIG. 8 depicts a cross-sectional view of the cutting tool 460 disposed within the cutting block 432. In particular, the cutting tool 460 has a smooth shaft 466 that extends to the depth 432a of the cutting block 432 and a cutting burr section 464 that extends into the bone to a pre-determined depth 470. The pre-determined depth of the bone can be determined as desired. For example, the depth of the bone can be determined as necessary to remove an impingement surface, or may be determined as necessary to provide an implant to mate with resurfaced bone or a bone from which cartilage has been removed. More precise milling and burring for the creation of an implant location could be done for example in a knee, hip, shoulder or other bone resection process. In those cases, the bone geometry can be fashioned so that the area 472 is structured as necessary to receive the implant.

As shown, the block 432 and the bone 468 mate along a conforming interface 502. The block is prepared according to patient-matched techniques so that the block and bone interface 502 is as precise as possible, thereby providing a closer and more accurate alignment site for the cutting tool 460.

Figure 9A:
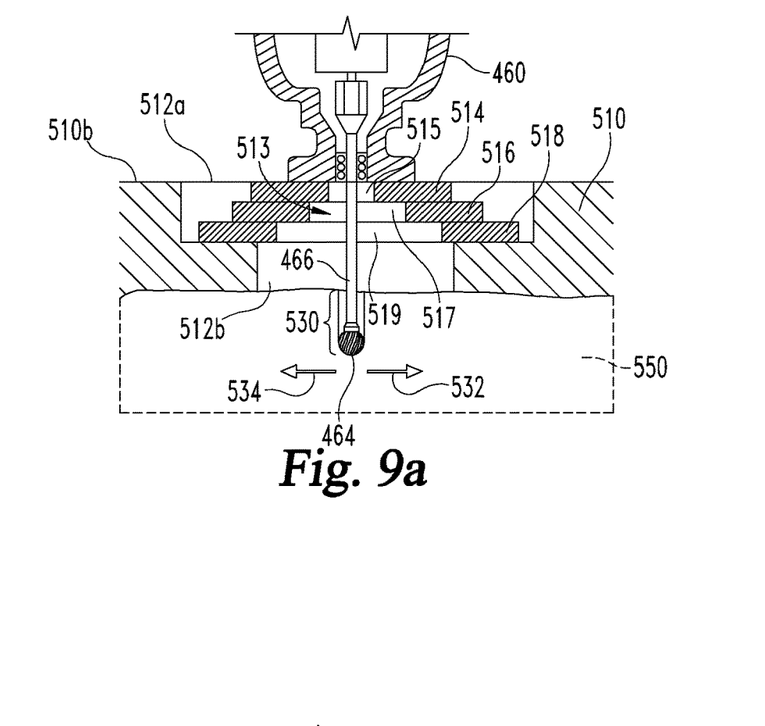
FIGS. 9A-9C depict an embodiment of a bone cutting system having a cutting block with a plurality of inserts that guide the movement of a burring or milling tool.
Figure 9B:
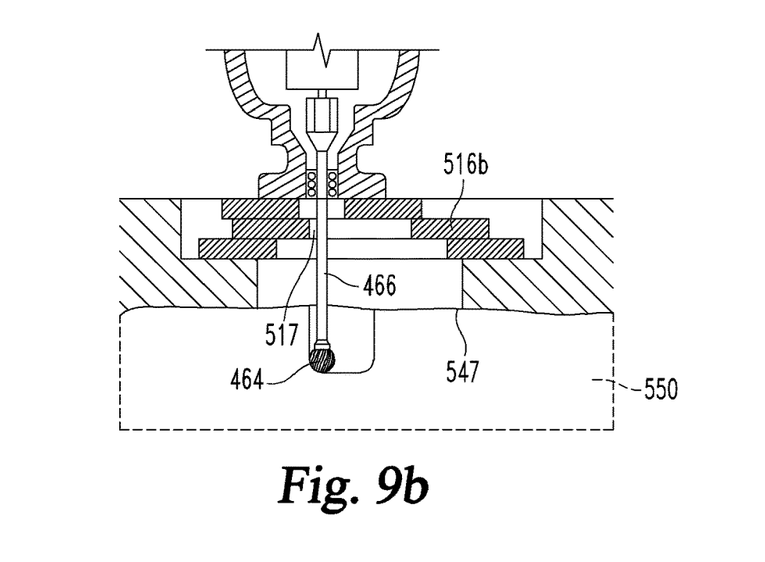
Figure 9C:
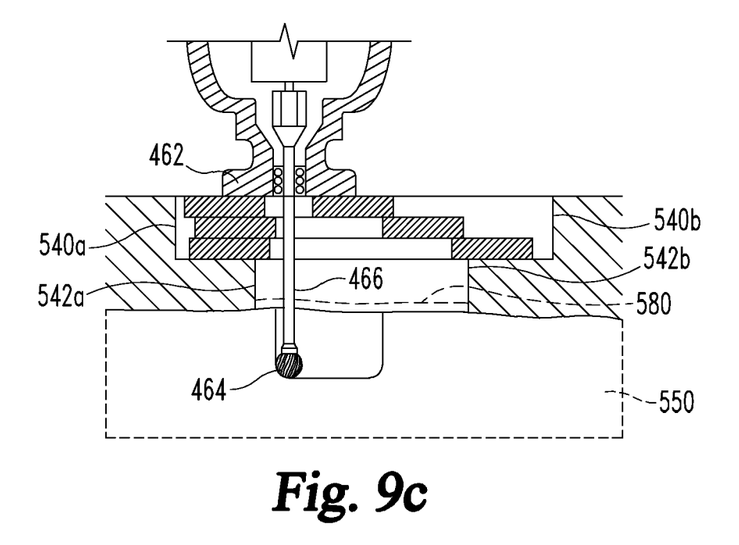

FIGS. 9A-9C depict other implementations of a patient-matched cutting guide system that can be adjusted to alter the location and lateral reach and depth of the milling or burring tool. In particular, the patient matched cutting block 510 is provided with a lower surface 510a that is configured with a plurality of surface regions with characteristics that correspond with specific surface features of the bone 550. The interface between bone and block, as described above, can be formed through patient-matched computer assisted techniques so that the block and the bone mate together as closely as possible. The cutting block 510 includes an opening having an upper portion 512a and a lower portion 512b, and a plurality of washer inserts 514, 516 and 518 that sit within the upper portion 512a and have respective inner openings (515, 517 and 519) that align above the lower portion 512b, forming a cutting guide track 513. The cutting tool 460 has a shaft 466 and a burr cutting distal tip 464. The burr cutting tip 464 is shown in FIG. 9A as being burrowed into the slot 530 in the bone 550. The shaft 466 extends through the lower portion 512b of the track 513 and through the openings 515, 517, and 519 of the washer inserts 514, 516, and 518. As shown in FIGS. 9A-9C, the burr cutting member can be extended laterally in direction arrows 532 and 534 when inserted into the bone, to create a suitable resection area within the bone for subsequent reception of an implant or for general resurfacing.

The stacked washers 514, 516, and 518 allow a surgeon to cut slot 530 to a controlled height that would be difficult to cut using only cutting tool 460 and cutting block 510. The disc 462 on cutting tool 460 is narrower than the width 580 of the lower portion 512b of the opening in cutting block 510, and thus the disc 462 would not maintain the tool 460 at the height of upper boundary surface 510b if washer inserts were not used. Instead, the cutting tool 460 would be free to lower all the way into the cutting block 510 until the disc 462 contacts the bone 550. The resulting cut would be much deeper than the controlled height shown in slot 530 and could lead to serious complications. The washers 514, 516, and 518 are used to provide a platform that maintains the cutting tool 460 at the desired level of upper boundary surface 510b to allow cut to be made with a controlled height across the full width 580 of the lower portion 512b of the cutting block 510.

The washer inserts 514, 516, and 518 of the system of FIGS. 9A-9C can move laterally within the guide track 513 to control the lateral motion of the burr cutting tool 460. As the cutting tool 460 is moved laterally in the direction of arrow 534, the shaft 466 contacts the washer 514. The washer 514 is free to move laterally, and the shaft 466 pushes the washer 514 in the direction of arrow 534 until the shaft 466 contacts washer 516, as shown in FIG. 9B. The shaft 466 then pushes the washer 516 in the direction of arrow 534 until the shaft 466 contacts washer 518, which it also pushes in the direction of arrow 534. The shaft 466 is then stopped when the washers 514, 516, and 518 contact the side wall 540a of the opening in the cutting block 510. In this position, the shaft 466 contacts the inner wall 542a of the cutting block 510, creating the left lateral boundary of the slot 530 cut into the bone 550. The cutting tool 460 is then moved in the opposite direction, indicated by arrow 532 in FIG. 9A, until the washers 514, 516, and 518 contact the opposite side wall 540b and the shaft 466 contacts the opposite inner wall 542b. The lateral cut is then complete, and the slot 530 cut into the bone 550 spans the full width 580 of the lower portion 512b and is a uniform controlled height as the cutting tool 460 is maintained at the height of upper boundary surface 510b for the duration of the cut.

In the implementation shown, the washer members can be removed and replaced, and altered (in terms of their size and the size of their openings) as desired to customize the depth and lateral reach of the cutting tool. In certain implementations, one or more such washer members can be used instead of the disc 462 of the cutting tool, thus allowing more flexibility to extend the cutting tool 460 laterally and depth wise with respect to the bone.

Systems and methods provide patient-specific cutting blocks that allow for bone resurfacing procedures, such as milling or burring, with simplified devices. A computer assisted surgical cutting block is produced having a surface region that matches with the surface region of a patient's bone to be altered. A cutting tool may be provided having a contoured bone mating surface and a contoured and patient-specific shaped cutting guide surface, which is located in a plane above the bone mating surface. One or more channels are provided in the cutting block, and as the surgeon moves the cutting tool (a milling or burring, for example) in the channels the tool cuts the bone both laterally along the surface of the bone and vertically into the bone according to preselected the cutting guide surface and other surface features of the cutting block. Variations and modifications will occur to those of skill in the art after reviewing this disclosure. The disclosed features may be implemented, in any combination and sub combinations (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A method, comprising:
receiving information relating to an image representative of a surface of a bone, the image identifying a plurality of surface characteristics of the bone, wherein each surface characteristic comprises one or more of a contour, a slope, and a landmark;
receiving information relating to a region of the bone surface to be removed from the bone;
receiving information relating to a desired configuration of the bone surface, the desired configuration including at least one contour; and
generating a cutting guide model based at least in part upon the received information, wherein generating the cutting guide model comprises:
generating an upper surface, wherein the upper surface comprises a contoured configuration corresponding to the desired configuration of the bone surface;
generating an interior surface, wherein the interior surface comprises a plurality of surface features, and wherein each surface feature corresponds to one of the surface characteristics of the bone;

generating a side surface, wherein the side surface at least partially defines an outer perimeter of the cutting guide model;

generating an entry port having a first entry port section formed in the side surface, wherein the entry port interrupts the outer perimeter of the cutting guide model; and generating a channel extending between the upper surface and the interior surface, wherein the channel is connected to the first entry port section and defines a cutting path corresponding to the region of the bone surface to be removed from the bone.

2. The method of claim 1, further comprising manufacturing a cutting guide based on the cutting guide model.

3. The method of claim 1, wherein the entry port further includes a second entry port section, wherein the first entry port section has a first width, wherein the second entry port section has a second width, and wherein the second width is greater than the first width.

4. The method of claim 3, further comprising receiving information relating to a cutting tool having a shaft and a rotary tip, wherein the first width corresponds to a dimension of the shaft, and wherein the second width corresponds to a dimension of the rotary tip.

5. The method of claim 4, wherein the channel has the first width.

6. The method of claim 5, wherein the channel includes a plurality of parallel channel sections, wherein each of the channel sections has a center line, and wherein a distance between the centerlines of adjacent channel sections is less than the dimension of the rotary tip.

7. The method of claim 4, wherein the entry port is sized and configured to receive the cutting tool in a direction transverse to a longitudinal axis of the shaft.

8. The method of claim 1, wherein generating the cutting guide model further comprises generating an exit port having a first exit port section formed in the side surface, wherein the exit port interrupts the outer perimeter of the cutting guide model, and wherein the channel is further connected to the exit port.

9. The method of claim 8, wherein the channel defines the cutting path as a single continuous path between the entry port and the exit port.

10. A method, comprising:
receiving an image of a surface of a bone, the image identifying a surface characteristic comprising one or more of a contour, a slope, and a landmark on the bone;
identifying a region of the bone surface to be removed from the bone;
determining a desired configuration of the bone surface, the desired configuration including at least one contour; and
generating a cutting guide based at least in part upon the image, wherein the cutting guide has a channel, an upper surface having a contoured configuration, and an interior surface with a plurality of surface features, each surface feature corresponding to a surface characteristic on the image, the contoured configuration corresponding to the desired configuration of the bone surface; and
wherein the cutting guide is structured such that when the cutting guide is applied to the bone and the surface features are aligned with the corresponding surface characteristics, the channel sits above and extends substantially to the region to be removed, and the channel is operable to receive a cutting tool such that the cutting tool contacts the region.

11. The method of claim 10, wherein the channel extends between the upper surface and the interior surface in a first direction, and wherein the channel extends through an outer perimeter of the cutting guide in a second direction transverse to the first direction.

12. The method of claim 11, wherein the channel defines a single continuous cutting path corresponding to the region of the bone surface to be removed from the bone.

13. The method of claim 10, wherein the cutting tool comprises a shaft and a rotary tip, wherein the cutting guide further comprises an entry port connected to the channel, wherein the entry port comprises a first entry port section structured to receive the shaft and a second entry port section structured to receive the rotary tip, and wherein a width of the second entry port section is greater than a width of the second entry port section.

14. A method of resecting a bone, comprising:
obtaining a cutting guide having a bone contacting inner surface and an upper surface with a contoured configuration, wherein the inner surface has one or more features configured to match a corresponding surface characteristic existing on the bone prior to cutting the bone, and wherein the contoured configuration corresponds to a desired bone surface configuration;
applying the cutting guide to the bone surface and matching each of the one or more features to the corresponding surface characteristic;
extending a cutting tool within the cutting guide along the contoured upper surface to cut the impinged bone surface according to the desired bone surface configuration;
passing the cutting tool within a channel of the guide; and
moving the cutting tool vertically within the channel along a slope of the upper surface.

15. The method of claim 14, further comprising a step of installing a removable washer within the channel.

16. The method of claim 15, further comprising a step of moving the cutting tool laterally along a surface of the bone within the channel.

17. The method of claim 15, further comprising a step of bracing a flange of the cutting tool against a surface of the cutting guide while cutting the bone.

18. The method of claim 15, further comprising a step of milling or burring the bone surface through the channel.

19. The method of claim 15, wherein the upper surface is spaced away from the inner surface.

20. The method of claim 15, further comprising a step of moving the washer within the channel.

* * * * *